United States Patent
Popescu

(10) Patent No.: US 8,005,185 B2
(45) Date of Patent: Aug. 23, 2011

(54) METHOD TO DETERMINE PHASE AND/OR AMPLITUDE BETWEEN INTERFERING, ADJACENT X-RAY BEAMS IN A DETECTOR PIXEL IN A TALBOT INTERFEROMETER

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 85 days.

(21) Appl. No.: 12/565,989

(22) Filed: Sep. 24, 2009

(65) Prior Publication Data

US 2010/0074395 A1    Mar. 25, 2010

(30) Foreign Application Priority Data

Sep. 24, 2008  (DE) .......................... 10 2008 048 683

(51) Int. Cl.
*A61B 6/00*        (2006.01)
(52) U.S. Cl. ................ 378/36; 378/19; 378/62
(58) Field of Classification Search .............. 378/36, 378/4, 16, 19, 62
See application file for complete search history.

(56) References Cited

U.S. PATENT DOCUMENTS 5,812,629 A * 9/1998 Clauser ........................ 378/62
7,433,444 B2 10/2008 Baumann et al.
2007/0153979 A1 7/2007 Baumann et al.
2009/0092227 A1 4/2009 David et al.

OTHER PUBLICATIONS

"X-ray Phase Imaging with a Grating Interferometer," Weitkamp et al. Optic Express, vol. 13, No. 16, pp. 6296-6304, (2005).
"Hard-X-ray Dark-Field Imaging Using a Grating Interferometer," Pfeiffer et al., Nature Materials, vol. 7 (2008), pp. 134-137.
"Phase-Measurement Interferometry Techniques," Creath, Progress in Optics XXVI (1988) pp. 349-393.

* cited by examiner

*Primary Examiner* — Chih-Cheng G Kao
(74) *Attorney, Agent, or Firm* — Schiff Hardin LLP

(57) ABSTRACT

In a method to determine phase and/or amplitude between interfering, adjacent x-ray beams in a detector pixel in a Talbot interferometer for projective and tomographical x-ray phase contrast imaging and/or x-ray dark field imaging, after an irradiation of the examination subject with at least two coherent or quasi-coherent x-rays, an interference of the at least two coherent or quasi-coherent x-rays with the aid of an irradiated phase grating is generated, and the variation of multiple intensity measurements in temporal succession after an analysis grating is determined in relation to known displacements of one of the gratings or of an x-ray source fashioned like a grating, positioned upstream in the beam path, relative to one of the gratings. The integrating intensity measurements ensue during a relative movement—thus not during the standstill—of one of the upstream gratings or of the x-ray source fashioned like a grating or of the examination subject, with known speed behavior over a final time interval of a final distance.

18 Claims, 3 Drawing Sheets

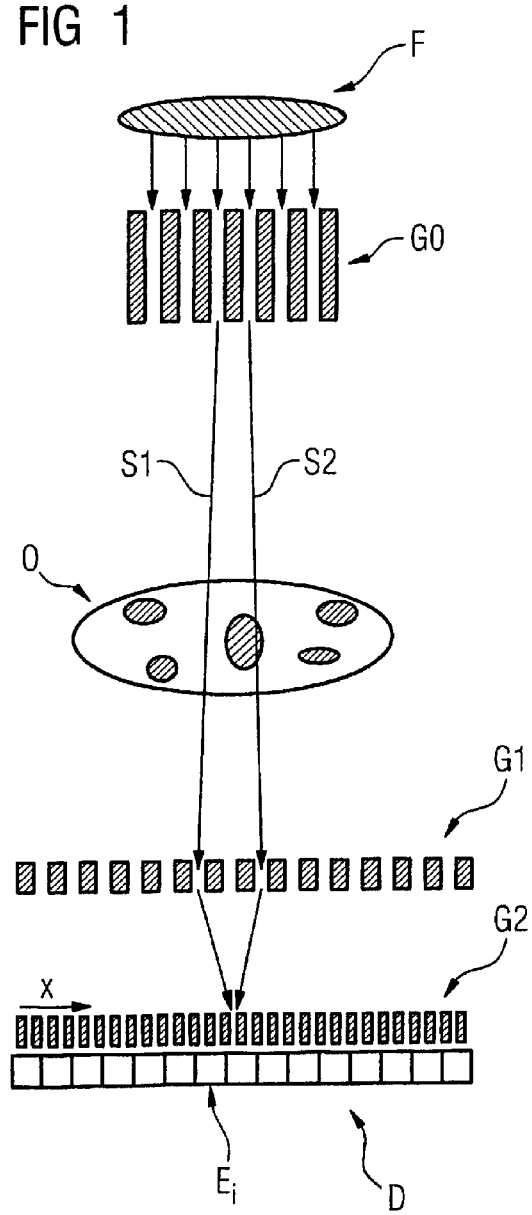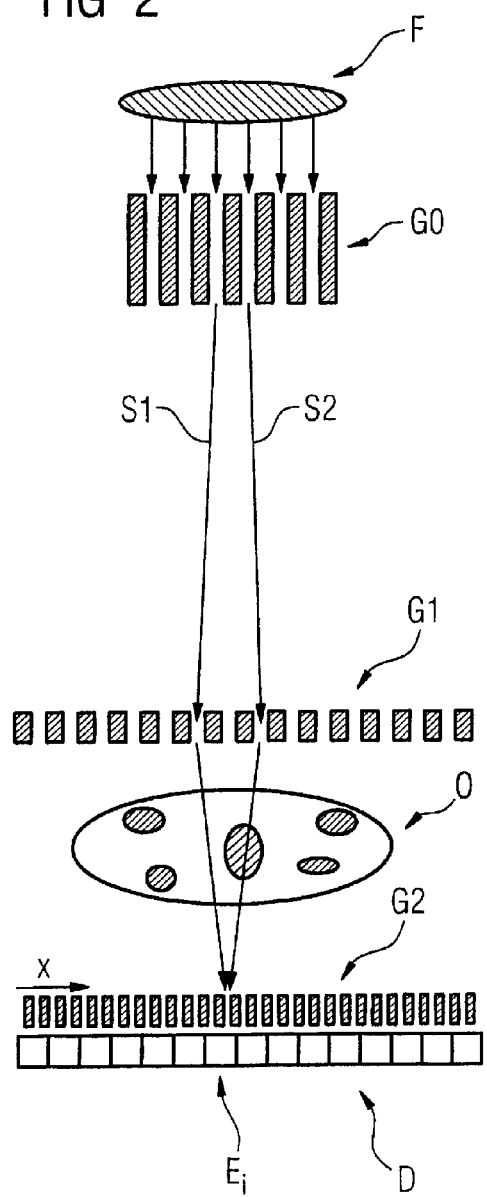

$$I(x) = I_{med} + I_{amp} \cos(x+x_0)$$

$$I_{sweep}(x_n, \Delta x) = I_{med} + I_{amp} \frac{\sin(\Delta x/2)}{\Delta x/2} \cos(x_n + x_0)$$

METHOD TO DETERMINE PHASE AND/OR AMPLITUDE BETWEEN INTERFERING, ADJACENT X-RAY BEAMS IN A DETECTOR PIXEL IN A TALBOT INTERFEROMETER

BACKGROUND OF THE INVENTION

1. Field of the Invention

The invention concerns a method to determine phase and/or amplitude between interfering, adjacent x-ray beams in a detector pixel in a Talbot interferometer for projective and tomographical x-ray phase contrast and/or x-ray dark field imaging.

2. Description of the Prior Art

It is known to determine phase and/or amplitude between interfering adjacent x-ray beams in a detector pixel in a Talbot interferometer for projective and tomographical x-ray phase contrast and/or x-ray dark field imaging by producing, after an irradiation of the examination subject with at least two coherent or quasi-coherent x-ray beams—an interference of the two coherent or quasi-coherent x-ray beams using an exposed phase grating, and the variation of multiple intensity measurements in temporal succession after an analysis grating is determined in relation to known relative shifts of a grating positioned in the beam path or of an x-ray source fashioned like a grating, relative to one or more of the gratings.

Similar methods to determine phase and amplitude between interfering, adjacent x-ray beams in a detector pixel are generally known. The disclosure document DE 10 2006 037 255 A1 is referenced as an example. In this document (in particular in FIGS. 1 and 2 with associated description) it is shown how the intensity curve of a detector pixel is to be measured depending on the displacement of an upstream x-ray grating in order to determine the relative phase shift of x-rays between two adjacent detector pixels. A grating upstream of a detector pixel is sequentially displaced perpendicular to the grating alignment, wherein at every displaced position the radiation intensity occurring at the detector pixel is measured. The intensity curve across the grating positions can be determined via at least three measurements at different grating positions, and the phase can therefore be calculated.

A significant problem in this type of measurement is that a sequential displacement of one of the gratings must occur. This means that the grating is displaced by a specific amount, and an integrating measurement of the radiation intensity at the detector pixel is subsequently implemented in a final time period, whereupon a displacement of the grating with subsequent measurement at an unmoved grating occurs again. This cycle is repeated until the maximum available shift of the grating is achieved. In the case of the examination of a patient, in order to minimize the patient dose the radiation source is alternatively switched on and off so that radiation is emitted toward the patient only during the integration time of the detector, thus when the grating is stationary and the actual measurement ensues. Such a method is very complicated and generates relatively long sampling measurement times, so it is difficult to integrate these measurement procedures into practical applications, in particular into fast CT scans with a rotating gantry.

Another possibility of direct measurement of phase and amplitude of the intensity curve of the radiation after an analysis grating is described in DE 10 2006 017 290 A1. Here the combination of analysis grating and detector pixel is replaced by the detector pixel itself having a number of detection strips fashioned in grating line directions so that the phase and amplitude of the corresponding x-ray can be directly measured in a measurement session. However, such an arrangement is very complicated and, at the present time, is not suitable for designing the detector in quantity, due to cost reasons.

European Patent Application EP 1 803 398 A1 discloses that instead of an absorption grating arranged at the source, an x-ray source is executed in a band shape that achieves the same effect as a source grating downstream of the focus. This variant of an x-ray source is also usable in connection with the present method, with the displacement of the bands imitating x-rays on the anode being equated with the displacement of the source grating.

An additional method, in which the knowledge of the intensity curve of x-ray radiation after an analysis grating is necessary, is dark field imaging with hard x-rays. Reference is made in this regard to the publication by F. Pfeiffer et al., "Hard X-ray dark field imaging using a grating interferometer", Nature Materials Vol. 7, Pages 15 through 137, 1 Feb. 2008. This document describes how an x-ray dark field imaging (similar to dark field imaging from optical microscopy) is possible, wherein the information of the direct x-ray radiation is masked out using a grating interferometer and only the information of the scatter radiation is used for imaging. It is necessary to know the intensity curve depending on the displacement of an analysis grating in a detector pixel in order to determine the amplitude of the intensity curve on the basis of the measured intensity curve. Not only the phase information but also the amplitude information is used for imaging. In principle, a corresponding measurement of the intensity curve of the detector pixel is necessary depending on the displacement of an upstream grating. A sequential displacement of the grating and measurement at a stationary grating have also been previously implemented in this context. The difficulties that result due to such a sequential measurement correspond to the difficulties that occur in phase contrast measurement.

SUMMARY OF THE INVENTION

An object of the present invention is to provide a method to measure the intensity curve at a detector pixel relative to the displacement of the upstream grating in a Talbot interferometer that delivers the desired information (such as phase, amplitude or intensity median) in a simplified manner.

The invention is based on the insight that it is possible to exactly describe the desired properties of an intensity curve at a detector pixel depending on the displacement of an upstream grating in a grating interferometer without a stoppage during the measurement being necessary, with the prerequisite of knowledge of the movement function of the upstream grating that is moved. In principle, different mathematical methods can be used of this purpose, so that ultimately a knowledge of the movement of the upstream grating to the measurement values is obtained so that the acquired median values of an integrating intensity measurement is implemented over a distance of the grating movement, and the known path-time relationship of the grating is taken into account.

In the simplest case of a linear movement of a grating with grating webs fashioned as rectangles—thus a movement of the grating with constant speed $v(x)$=constant during the measurement cycle—the correlation between an median measured intensity value $I_{sweep}(x, \Delta x)$ during the integration period of $x-\Delta x/2$ to $x+\Delta x/2$ and the differential curve of the intensity $I(x)$ with $I(x)=I_{med}+I_{amp} \cos(x+x_0)$ can be described as follows:

$$I_{sweep}(x, \Delta x) = \frac{1}{\Delta x}\int_{x-\Delta x/2}^{x+\Delta x/2} (x)\,dx$$

$$= I_{med} + \frac{I_{amp}}{\Delta x}\left[\begin{array}{c}\sin\left(x+x_0+\frac{\Delta x}{2}\right)-\\ \sin\left(x+x_0-\frac{\Delta x}{2}\right)\end{array}\right] =$$

$$= I_{med} + I_{amp}\frac{\sin(\Delta x/2)}{\Delta x/2}\cos(x+x_0)$$

$I_{sweep}(x, \Delta x)$=integrated, median measurement value for the integration period of $x-\Delta x/2$ to $x+\Delta x/2$;
$I(x)$=actual intensity value at the displacement value x of the grating;
$I_{med}$=median intensity value around which the intensity sinusoidally fluctuates given displacement of the grating;
$I_{amp}$=amplitude of the sinusoidal fluctuation of the intensity values given displacement of the grating;
$\Delta x$=measurement interval of an integrated measurement;
x=displacement value of the grating;
$x_0$=phase position of the interference pattern.

Under consideration of the relation $I(x)=I_{med}+I_{amp}\cos(x+x_0)$, a factor of $$\frac{\sin(\Delta x/2)}{\Delta x/2}$$

then results between the measured amplitude value $I_{amp}^{meas}$ of the integrating, implemented measurements and corrected differential amplitude value $I_{corr}^{meas}$, and it applies that $$I_{amp}^{corr} = I_{amp}^{meas}\frac{\Delta x/2}{\sin(\Delta x/2)}.$$

If information can be learned as to the actual differential curve of the intensity, a corresponding correction of the measurement values is necessary and also possible. This is particularly necessary given measurements for the x-ray dark field imaging since here the imaging is essentially determined by the amplitude level $I_{amp}$.

It should be noted that the phase position of the intensity curve in integrating measurements experiences no variation during a continuous linear movement of the grating, if the measurement value of the integration period with a grating displaced from position $x-\Delta x/2$ to the position $x+\Delta x/2$ is associated with a virtual measurement with stationary grating at position x. The phase thus can be directly taken from the integrating measurements, assuming linear movement of the grating.

If the relation cited above between the median measured intensity value $I_{sweep}(t, \Delta t)$ and the differential curve of the intensity I(t) is considered not dependent on the grating path x, but rather on the time t, analog relationships arise due to the linear path/time relationship of the grating movement, with:

$$I_{sweep}(t, \Delta t) = \frac{1}{\Delta t}\int_{t-\Delta t/2}^{t+\Delta t/2}(t)\,dt$$

$$= I_{med} + \frac{I_{amp}}{v\Delta t}\left[\begin{array}{c}\sin\left(vt+x_0+\frac{v\Delta t}{2}\right)-\\ \sin\left(vt+x_0-\frac{v\Delta t}{2}\right)\end{array}\right] =$$

$$= I_{med} + I_{amp}\frac{\sin(v\Delta t/2)}{v\Delta t/2}\cos(vt+x_0)$$

An analog correction factor of $$\frac{\sin(v\Delta t/2)}{v\Delta t/2}$$

for the amplitude value of the integrating implemented measurements results under consideration of the relationship $I(t)=I_{med}+I_{amp}\cos(v\cdot t+x_0)$.

These analytical considerations implemented above can also be transferred to arbitrary path/time relationships, for example a sinusoidal movement of the grating, such that integrating measurement values can be correspondingly corrected with knowledge of the path/time relationship and the underlying differential intensity curve can be analytically determined from the measurement values.

Another variant to obtain the desired information—thus the phase position $x_0$ for an imaging on the basis of phase variations of adjacent x-ray radiation (thus for phase control representation); the median intensity $I_{med}$ for absorption representations, and the amplitude value of the differential intensity curve $I_{amp}$ for x-ray dark field imaging—from integrating intensity measurements and with knowledge of an arbitrary but known path/time relationship v(t) of the grating movement is described as follows:

The sinusoidal oscillation of the intensity as a function of the grating position of a grating in the interferometer can be described with:

$$I(x)=I_{med}+I_{amp}\cos(x+x_0)$$

or, analogously formulated depending on time, with:

$$I(t)=I_{med}+I_{amp}\cos(vt+x_0).$$

The intensity value of an integrating measurement $I_{sweep}(t_1, t_2)$ between the points in time $t_1$ and $t_2$ can be represented with:

$$I_{sweep}(t_2, t_1) = \frac{1}{t_2-t_1}\int_{t_1}^{t_2}I(t)\,dt$$

$$= I_{med} + \frac{I_{amp}}{t_2-t_1}\int_{t_1}^{t_2}\cos(v(t)\cdot t+x_0)\,dt$$

or equivalently with:

$$I_{sweep}(t_2, t_1) =$$

$$I_{med} + \frac{I_{amp}\cos(x_0)'^2}{t_2-t_1}\int_{t_1}^{t_2}\cos(v(t)\cdot t)dt - \frac{I_{amp}\sin(x_0)'^2}{t_2-t_1}\int_{t_1}^{t_2}\sin(v(t)\cdot t)dt$$

The path/time relationship v(t) of the grating can advantageously be directly detected by means of a position transmitter at the grating. In a preferred exemplary embodiment, the position detection can now store the measured value pair (x, t) (consisting of the x position of the grating and its measurement time t) in a table in real time. The sampling of the grating position should thereby be faster than the integration time of the detector. Since the path/time relationship v(t) of the grating is now known, the integrals $$J_{cos} = \int_{t_1}^{t_2}\cos(v(t)\cdot t)\,dt \text{ and } J_{sin}$$

$$= -\int_{t_1}^{t_2}\sin(v(t)\cdot t)\,dt$$

are numerically calculated, and for every measurement in the new relationship $$I_{sweep}^i = A+B+J_{cos}^i+C\cdot J_{sin}^i \text{ with } i=1\ldots N$$

can be described, wherein the three new unknowns $$A = I_{med}, B = I_{amp}\cos(x_0) \text{ and } C = I_{amp}\sin(x_0)$$

correspond.

If at least three measurements exist, these unknowns A, B and C (and therefore also the sought information) can be analytically calculated. A numerical method, for example a "least square fit" method can likewise be implemented for this, advantageously using a larger number of measurement values.

Based on the above, the invention concerns improving a method to determine phase and/or amplitude and/or median value of an intensity curve of interfering, adjacent x-ray beams after an analysis grating depending on a relative displacement of a grating or of an examination subject, the phase and/or amplitude and/or median value or values being determined in a detector pixel in an x-ray grating interferometer or x-ray phase contrast CT or x-ray dark field radiography system. It is known that an irradiation of the examination subject occurs with at least two coherent or quasi-coherent x-ray beams; an interference of the at least two coherent or quasi-coherent x-ray beams is generated with the aid of an exposed phase grating; and a determination is implemented of properties of the intensity curve of interfering x-ray radiation after an analysis grating in relation to known displacements of a grating upstream in the beam path or of an x-ray source fashioned like a grating relative to the grating or the other gratings, wherein at least three integrating intensity measurements are implemented to determine the properties of the intensity curve.

According to the invention, the integrating measurements ensues during a relative movement (thus not during the standstill) of one of the upstream gratings, or of the x-ray source fashioned like a grating, or of the examination subject with known speed behavior over a final time interval or a final distance. It is thus not necessary, however, to keep the gratings at rest relative to one another for intensity measurement; rather, an intensity measurement can be implemented while the gratings move, wherein the knowledge of the speed relationship or, respectively, path-time relationship of the grating during the measurement interval is necessary for this purpose.

For example, a uniformly linear movement continuing over at least one time period during the movement can be used as a relative movement for one of the upstream gratings or for the x-ray source fashioned like a grating or for the examination subject. A linear movement continuing over at least one time period is advantageously used that is part of a back-and-forth movement over a number of time periods. A movement function is thus used that moves the respective grating to be moved back and forth in alternation with identical speed between two n points. The measurement occurs in the times of uniform movement.

If such a linear movement is used, an association of the integrated intensity measurement value with a specific grating position of the upstream grating or of the x-ray source fashioned like a grating or of the examination subject can occur under consideration of the known speed relationship (thus the known constant speed). If the known speed relationship is a uniformly linear movement, the median value of the displacement between the beginning and end of the integration value can be selected in the association of the integrated intensity measurement value with the displacement value of the upstream grating or of the x-ray source fashioned like a grating or of the examination subject.

The possibility also exists to calculate the actual intensity curve I(x) of the integrated intensity measurement values $I_{sweep}(x, \Delta x)$ according to the following equation:

$$I(x) = I_{med} + \frac{I_{sweep}(x, \Delta x) - I_{med}}{\frac{\sin(\Delta x/2)}{\Delta x/2}}$$

wherein:
$I_{med}$ = median value of the intensity curve calculated as the median value of the measured intensity measurement values $I_{sweep}(x, \Delta x)$,
$I_{amp}$ = amplitude of the intensity curve $I(x) = I_{med} + I_{amp}\cos(x + x_0)$,
x = median grating position during the measurement,
$\Delta x$ = integration interval of a measurement,
$x_0$ = sought phase position.

It is noted that only the phase shift between two adjacent x-ray beams must be calculated to generate phase contrast images, while only the amplitude level and the median value of the intensity curve need to be determined for imaging according to a dark field radiography.

In another variant of the method according to the invention a predetermined movement curve with a speed profile is used as a relative movement for one of the upstream gratings or for the x-ray source fashioned like a grating or for the examination subject, and the (differential) intensity curve is calculated by solving an equation system with at least N equations and N unknowns on the basis of the integrated intensity measurement values under consideration of the speed profile.

The following equation system can be used for this calculation:

$$I_{sweep}(t_1, \Delta t) = A + B \cdot J_{cos}(t_1, \Delta t) + C \cdot J_{sin}(t_1, \Delta t)$$
$$I_{sweep}(t_2, \Delta t) = A + B \cdot J_{cos}(t_2, \Delta t) + C \cdot J_{sin}(t_2, \Delta t)$$
$$I_{sweep}(t_3, \Delta t) = A + B \cdot J_{cos}(t_3, \Delta t) + C \cdot J_{sin}(t_3, \Delta t)$$

with $$J_{cos}(t_i, \Delta t) = \frac{\int_{t_i - \Delta t/2}^{t_i + \Delta t/2} \cos(v(t) \cdot t) dt}{\Delta t}$$

$$J_{sin}(t_i, \Delta t) = \frac{\int_{t_i - \Delta t/2}^{t_i + \Delta t/2} \sin(v(t) \cdot t) dt}{\Delta t}$$

$$A = I_{med}$$
$$B = I_{amp}\cos(x_0)$$
$$C = I_{amp}\sin(x_0)$$

wherein:
$I_{sweep}(t_i, \Delta t)$ = integrated intensity measurement value around the point in time $t_i$ with the measurement interval $\Delta t$,
$I_{med}$ = sought median value of the intensity,
$I_{amp}$ = sought amplitude portion of the differential intensity values,
x = displacement of the grating,
$x_0$ = sought phase shift.

This equation system can be solved via an analytical calculation (thus exactly), or the possibility exists to calculate this equation system through numerical methods. An overdetermined equation system is advantageously used for this. More measurement values than unknowns are thus evaluated (advantageously in a numerical calculation) so that errors during the measurement can be compensated. For example, this can be implemented via a "least square fit" method with the aforementioned equation system.

For completeness it is noted that, in principle, it is possible not only to move the analysis grating, but also a movement of the phase grating or of the source grating, or even of the x-ray source fashioned like a grating, or even of the examination subject, is possible in order to implement the method described in the preceding.

Furthermore, it is noted that the invention also encompasses an x-ray grating interferometer, an x-ray phase contrast imaging system and a system for projective and/or tomographical x-ray dark field imaging. Such a system has a computer that controls the measurement procedure, the computer having a program memory in which a program or program module is stored that causes the method according to one of the embodiments described above to be implemented.

BRIEF DESCRIPTION OF THE DRAWINGS

FIG. 1 is a schematic representation of a grating interferometer for x-ray radiation with transmission gratings and source grating; the examination subject arranged between source grating and phase grating.

FIG. 2 is a schematic representation of a grating interferometer for x-ray radiation with transmission gratings and source grating; the examination subject arranged between phase grating and analysis grating.

DESCRIPTION OF THE PREFERRED EMBODIMENTS

Figure 3:
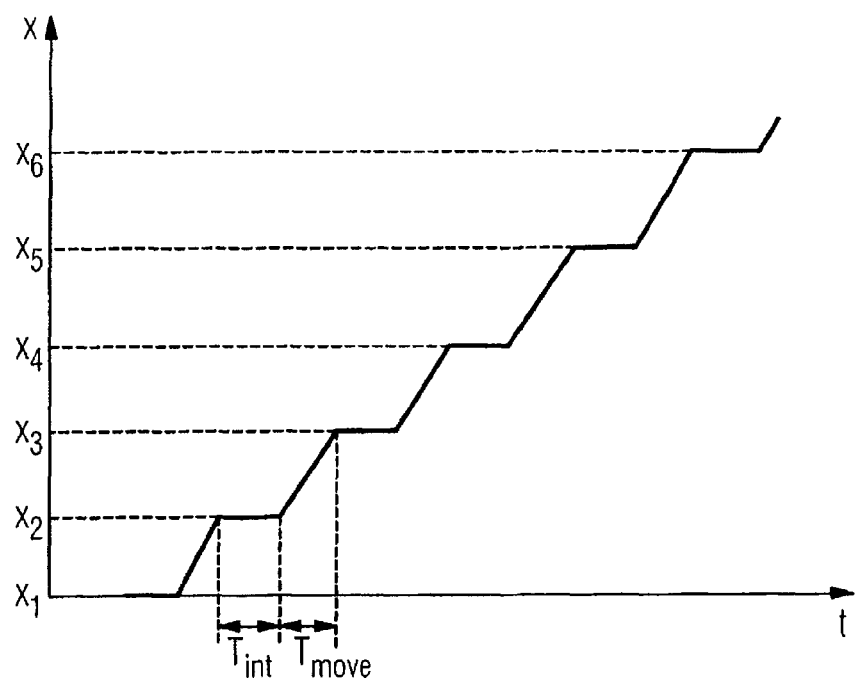
FIG. 3 shows a path/time curve of a grating give sequential x-ray phase contrast measurement or x-ray dark field measurement.

In the following the invention is described in detail using the preferred exemplary embodiments with the aid of Figures, wherein only the features necessary for understanding the invention are shown. The following reference characters and variables are hereby used: $I_{amp}$: sought amplitude portion of the differential intensity values; $I_{med}$: sought median value of the intensity; $I_{sweep}(t, \Delta t)$, $I_{sweep}(x_i, \Delta x)$: integrated intensity measurement value around the point in time $t_i$ or the position $x_i$ with the measurement interval $\Delta t$ or, respectively, $\Delta x$; $\Delta x$, $\Delta t$: measurement interval with regard to the grating movement or, respectively, with regard to the measurement time; D: detector; $E_i$: detector elements; F: focus of a radiation source; G0: source grating; G1: phase grating; G2: analysis grating; I(x): differential intensity curve; O: examination subject; S1, S2: x-ray beams; t: time; $T_{int}$: time interval of the integration for measurement; $T_{move}$: time interval of the positioning of the grating; x: displacement path of a grating or of a grating-like x-ray source or of an examination subject; $x_0$: phase; $x_1$ through $x_6$: grating position.

FIGS. 1 and 2 show two different configurations of grating interferometers, respectively with a large-area focus F as an x-ray source and a subsequently arranged source grating G0 in which quasi-coherent x-ray beams are radiated in bands at the gaps of the source grating G0 while they are suppressed in the range of the absorption of the webs of the grating. Two adjacent, coherent x-ray beams S1 and S2 are respectively shown as examples that strike a phase grating G1 in the beam course, in which phase grating G1 a diffraction of the beams occurs so that following the phase grating G1 an interference pattern of the diffracted x-ray radiation arises. To make this interference pattern visible, a third grating (the analysis grating G2) is used which is upstream of a detector D with a plurality of detector elements $E_i$. Due to the interaction of the periodic interferences of the x-ray radiation with the analysis grating G2, an intensity fluctuation of the passing x-ray radiation results after the analysis grating depending on the position of said analysis grating G2, which interference fluctuation can be measured at the individual detector elements depending on the displacement of the grating G2, or also on displacements of the upstream gratings. The difference between the two systems shown in FIGS. 1 and 2 is that, in FIG. 1, the subject O to be examined is arranged between the source grating G0 and the phase grating G1, while in FIG. 2 the subject to be examined is positioned between the phase grating G1 and the subsequent analysis grating G2. In principle, a higher spatial resolution is achieved by the variant of FIG. 2 relative to the variant of FIG. 1.

Figure 4:
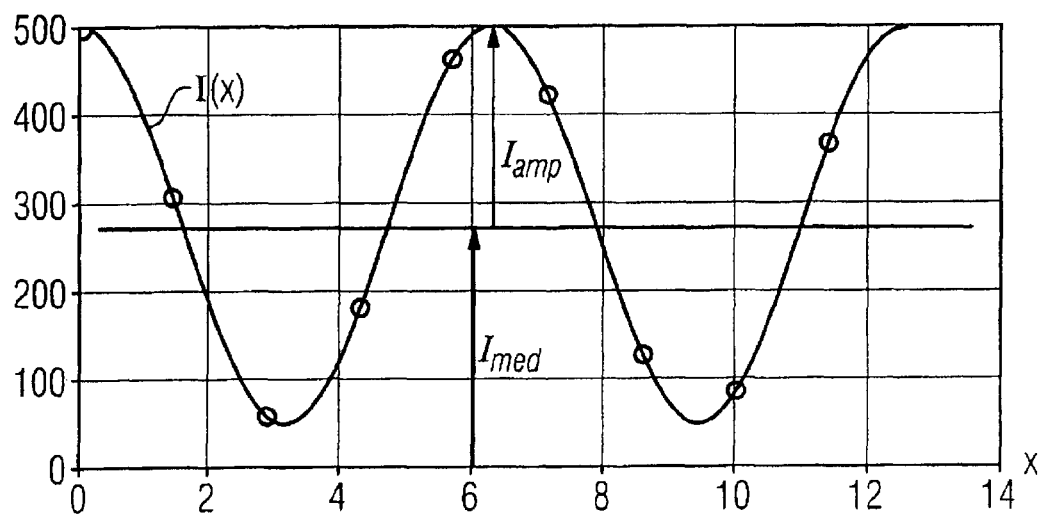
FIG. 4 shows a differential curve of the x-ray intensity at a detector pixel after the phase grating in relation to the relative displacement of a grating or of the examination subject, with measurement points given sequential measurement.

If the effect of the displacement of one of the gratings in the x-direction on the intensity measurement of a detector element is considered, a differential intensity curve results depending on the grating deflection or, respectively, grating displacement x as it is shown in FIG. 4 as an intensity curve I(x) in the form of a sinusoidal oscillation. This curve can be completely described by the specification of the median value $I_{med}$, the specification of the deflection amplitude $I_{amp}$ and the phase $x_0$ with which the sinusoidal deflection runs.

Corresponding to the known prior art, the course of the intensity curve is determined depending on the displacement of a grating by a sequential displacement of the grating to different grating positions and stationary measurement of the radiation intensity at the grating positions.

Such a situation is presented in FIG. 3, in which the position x of the grating is plotted relative to the time curve t. It is shown that this position is maintained over a certain time period $T_{int}$ (thus the integration time period in the measurement) at the selected grating positions $x_1$ through $x_6$ while the grating is displaced from a position $x_n$ to the position $x_{n+1}$ during the time period $T_{move}$. It is easily recognizable that relatively long measurement times are necessary in this method, and moreover inaccuracies in the positioning of the grating can occur at the individual grating positions.

In the case of an examination of a living examination subject (such as a patient) it is necessary to keep the radiation exposure of the examination subject as low as possible. For this the radiation source can be switched on and off sequentially, in synch with the integration time in the intensity measurement at the detector. Radiation emission at the radiation source hereby occurs only at the time of the actual measurement, thus given a relative standstill of the grating and during the integration time $T_{int}$. The radiation remains switched off in the remaining time $T_{move}$ in which the grating is shifted from measurement position to measurement position.

According to the invention, the time problem generated by the continuous positioning and sequential measurement of the radiation intensity is solved by, instead of executing a stepped curve of the movement (as is shown in FIG. 3), the movement of the grating progresses continuously while at the same time a number of measurements are conducted over small measurement time periods. This new approach to the measurement method also advantageously allows an uninterrupted exposure since practically no down times arise in the measurement. The method can accordingly also now be implemented significantly more quickly, and most of all during the continuous rotation of the gantry.

Figure 5:
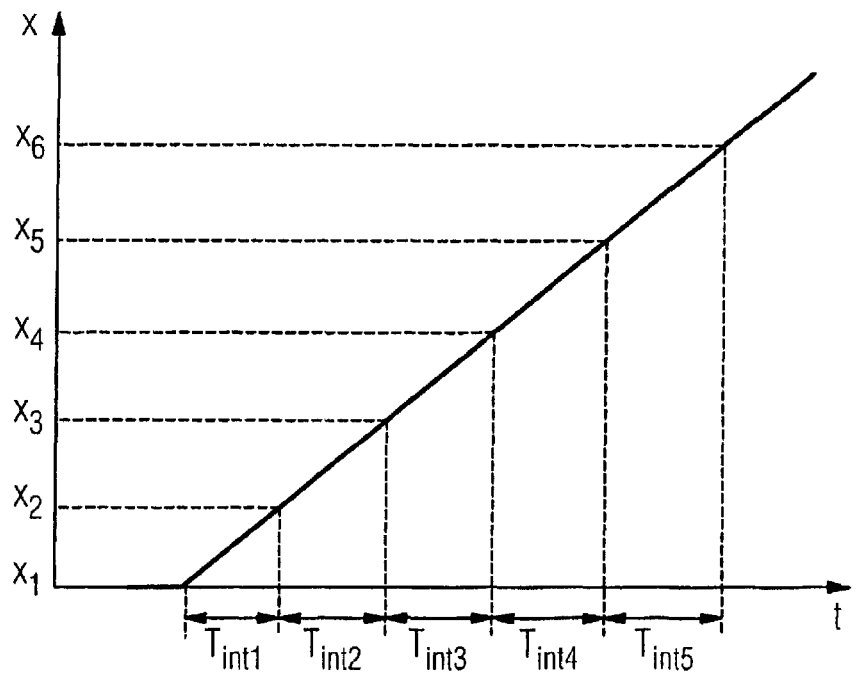
FIG. 5 shows a path/time curve of a grating given continuous x-ray phase contrast measurement or x-ray dark field measurement according to the invention.

Such a situation of the movement of the grating with linear speed is exemplarily shown in FIG. 5. Here the movement of the grating across the positions $x_1$ through $x_6$ is plotted over time, wherein measurement intervals $T_{int1}$ through $T_{int5}$ in which the integrating intensity measurement of the detector is implemented are shown between the individual grating positions $x_1$ through $x_6$. In these measurement intervals the radiation now remains continuously active and is no longer switched on and off, as this was the case in the sequential measurement from FIGS. 3 and 4.

A problem with this type of measurement is that the signal that occurs at the detector element is no longer constant during the measurement period but rather varies continuously. The path/time function of the grating is known, however, so a correct association of the measured values with corresponding grating positions is possible via corresponding consideration of this path/time function in the evaluation of the measurement values. This means that a grating position is thus associated in that the median value of the measurement corresponds to the differential value of the intensity curve, corresponding to the known movement information. Alternatively, it would also be possible to correspondingly correct the measured intensity value and in this way to bring about a correct association between the measured position, or the median position of the measurement interval, and the differential intensity value.

Figure 6:
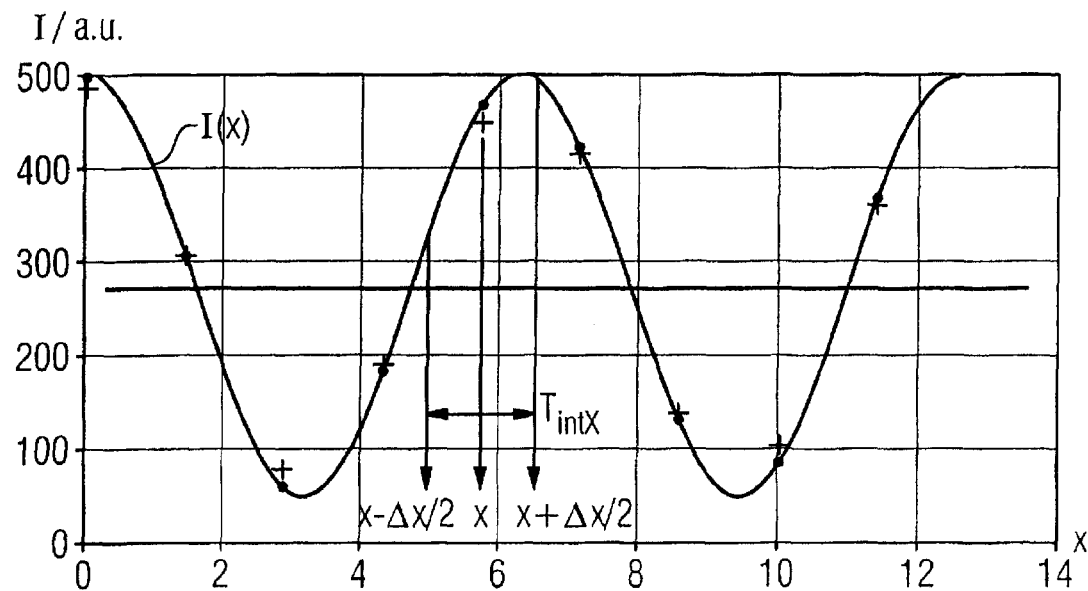
FIG. 6 shows a differential curve of the x-ray intensity at a detector pixel after the phase grating in relation to the relative displacement of a grating or of the examination subject with measurement points given continuous measurement.

FIG. 6 shows the type of measurement according to the invention on the basis of a grating moving continuously during the integrating intensity measurements. The differential intensity curve I(x) depending on the grating deflection x is represented with the sinusoidal line. While the radiation intensity varies sinusoidally due to the continuous movement of a grating upstream of the considered detector element, an integrating measurement is conducted at time intervals $T_{intx}$ that also correspond to a displacement interval $x-\Delta x/2$ through $x+\Delta x/2$ around a grating position x. As a result the values designated with "+" signs are obtained that, however, for the most part do not correspond to the actual values on the curve I(x). The correct values are represented by points on the curve I(x) at the respective position.

According to the invention, however, the possibility exists to extract the information desired for the respective application case from the differential intensity curve I(x) and from the integral measurement values as soon as the speed function of the moved grating is known. Among different application cases are:
  x-ray absorption imaging the median value $I_{med}$ of the differential intensity curve I(x) is required for this,
  x-ray phase contrast imaging knowledge of the phase $x_0$ of the differential intensity curve I(x) is sufficient for this; see also DE 10 2006 037 255 A1, and
  x-ray dark field imaging knowledge of the amplitude $I_{amp}$ and of the median value $I_{med}$ of the differential intensity curve I(x) is sufficient for this; see also in this regard F. Pfeiffer et al., "Hard X-ray dark field imaging using a grating interferometer".

Although modifications and changes may be suggested by those skilled in the art, it is the intention of the inventor to embody within the patent warranted hereon all changes and modifications as reasonably and properly come within the scope of his contribution to the art.

The invention claimed is:

1. A method to determine phase ($x_0$) and/or amplitude ($I_{amp}$) and/or median value ($I_{med}$) of an intensity curve I(x) of interfering, adjacent x-ray beams after an analysis grating depending on a relative displacement of a grating or of an examination subject in a detector pixel in an x-ray grating interferometer or x-ray phase contrast CT or an x-ray dark field radiography system, comprising the steps of:
  irradiating the examination subject with at least two coherent or quasi-coherent x-rays;
  generating of an interference of the at least two coherent or quasi-coherent x-rays with the aid of an irradiated phase grating;
  in a processor, determining properties of the intensity curve I(x) of interfering x-ray radiation after an analysis grating in relation to known relative displacements of a grating upstream or of the examination subject or of an x-ray source fashioned as a grating and positioned upstream in the beam path, said displacements being relative to at least one of the analysis grating, the grating upstream of the examination subject, or the x-ray source fashioned as a grating;
  executing at least three integrating intensity measurements to determine the properties of the intensity curve; and
  executing all integrating intensity measurements during a relative movement of one of the upstream gratings or of the subject or of the x-ray source fashioned as a grating with known speed behavior over a final time interval or a final distance.

2. A method as claimed in claim 1, comprising executing a uniformly linear movement over at least one time period as the relative movement for one of the upstream grating or of the examination subject or of the x-ray source fashioned as a grating.

3. A method as claimed in claim 2, comprising executing the linear movement over at least one time period as part of a back-and-forth movement over a plurality of time periods.

4. A method as claimed in claim 2, comprising associating values of the integrated intensity measurement curve (I(x)) respectively with displacement values (x) of the upstream grating or of the examination subject or of the x-ray source fashioned as a grating, dependent on the known speed behavior.

5. A method as claimed in claim 4, comprising selecting an average value (x) of the displacement between the beginning ($x-\Delta x$) and end ($x+\Delta x$) of the integration path ($x-\Delta x$ through $x+\Delta x$) given association of the integrated intensity measurement value with the displacement value of the upstream grating or of the examination subject or of the x-ray source fashioned as a grating.

6. A method as claimed in claim 2 comprising correcting the integrated intensity measurement values ($I_{sweep}(x, \Delta x)$) according to the following equation to determine the actual intensity curve (I(x)):

$$I(x) = I_{med} + \frac{I_{sweep}(x, \Delta x) - I_{med}}{\frac{\sin(\Delta x/2)}{\Delta x/2}}$$

wherein:
  $I_{med}$=median value of the intensity curve calculated as the median value of the measured intensity measurement values $I_{sweep}(x, \Delta x)$, $I_{amp}$=amplitude of the intensity curve $I(x)=I_{med}+I_{amp}\cos(x+x_0)$, x=median grating position during the measurement, Δx=integration interval of a measurement, $x_0$=sought phase position.

7. A method as claimed in claim 1, comprising:

executing a predetermined movement curve with a speed profile as the relative movement for one of the upstream grating or of the examination subject or for the x-ray source fashioned as a grating, and calculating the intensity curve (I(t) or I(x)) in the processor by solving an equation system with at least N equations and N unknowns on the basis of the integrated intensity measurement values under consideration of the measured speed profile.

8. A method as claimed in claim 7, comprising using the following as said equation system:

$$I_{sweep}(t_1, \Delta t) = A + B \cdot J_{cos}(t_1, \Delta t) + C \cdot J_{sin}(t_1, \Delta t)$$

$$I_{sweep}(t_2, \Delta t) = A + B \cdot J_{cos}(t_2, \Delta t) + C \cdot J_{sin}(t_2, \Delta t)$$

$$I_{sweep}(t_3, \Delta t) = A + B \cdot J_{cos}(t_3, \Delta t) + C \cdot J_{sin}(t_3, \Delta t)$$

with $$J_{cos}(t_i, \Delta t) = \frac{\int_{t_i-\Delta t/2}^{t_i+\Delta t/2} \cos(v(t) \cdot t)\, dt}{\Delta t}$$

$$J_{sin}(t_i, \Delta t) = \frac{\int_{t_i-\Delta t/2}^{t_i+\Delta t/2} \sin(v(t) \cdot t)\, dt}{\Delta t}$$

$$A = I_{med}$$

$$B = I_{amp}\cos(x_0)$$

$$C = I_{amp}\sin(x_0)$$

$I_{sweep}(t_i, \Delta t)$=integrated intensity measurement value around the point in time $t_i$ with the measurement interval Δt, $I_{med}$=sought median value of the intensity, $I_{amp}$=sought amplitude portion of the differential intensity values, x=displacement of the grating, $x_0$=sought phase shift.

9. A method as claimed in claim 8, comprising solving the equation system in said processor by analytical calculation.

10. A method as claimed in claim 9, comprising solving the equation system in said processor by numerical calculation.

11. A method as claimed in claim 7, comprising using an over-determined equation system in said processor.

12. A method as claimed in claim 1, comprising moving the analysis grating.

13. A method as claimed in claim 1, comprising moving the phase grating.

14. A method as claimed in claim 1, comprising irradiating the examination subject with an x-ray source comprising a source grid, as a grating upstream of the examination subject, and moving the source grating.

15. A method as claimed in claim 1, comprising moving the examination subject.

16. A method as claimed in claim 1, comprising moving the x-ray source fashioned as a grating.

17. A method as claimed in claim 1, comprising measuring the speed behavior with a position sensor.

18. X-ray grating interferometer possessing a computer to control a measurement process, characterized in that the computer comprises a program memory in which a program or program module is stored that executes the method according to any of the preceding method claims upon operation.

\* \* \* \* \*